United States Patent [19]

Shah

[11] Patent Number: 4,510,197

[45] Date of Patent: Apr. 9, 1985

[54] WATER VAPOR PERMEABLE PRESSURE SENSITIVE ADHESIVES INCORPORATING MODIFIED ACRYLATE COPOLYMERS

[75] Inventor: Kishore R. Shah, Chelmsford, Mass.

[73] Assignee: The Kendall Company, Boston, Mass.

[21] Appl. No.: 481,509

[22] Filed: Apr. 1, 1983

[51] Int. Cl.³ .................... B32B 00/00; C08F 226/10
[52] U.S. Cl. ..................................... 428/220; 128/82; 128/155; 128/156; 524/548; 526/264
[58] Field of Search ........................ 526/264; 524/548; 428/220, 336

[56] References Cited

U.S. PATENT DOCUMENTS

| | | | |
|---|---|---|---|
| 3,405,084 | 10/1968 | Bohac et al. | 526/264 |
| 3,690,937 | 9/1972 | Guse et al. | 526/264 |
| 3,725,122 | 4/1973 | Reinhard et al. | 526/264 |
| 3,728,148 | 4/1973 | Pietsch et al. | 526/264 |
| 4,164,614 | 8/1979 | Ames | 526/264 |

Primary Examiner—Harry Wong, Jr.
Attorney, Agent, or Firm—Frederick R. Cantor

[57] ABSTRACT

The present invention comprises a water vapor permeable, pressure-sensitive adhesive composition useful for surgical and medical bandage applications, and incorporating modified copolymers of butyl acrylate containing N-vinyl 2-pyrrolidone and acrylic acid. The present pressure-sensitive adhesive composition results in enhanced water vapor transmission rates, which may lead to a concomittant reduction in skin lesions that were previously attendant upon the accumulation of water under conventional inadequately permeable pressure-sensitive adhesive-coated surgical and medical dressings.

4 Claims, No Drawings

WATER VAPOR PERMEABLE PRESSURE SENSITIVE ADHESIVES INCORPORATING MODIFIED ACRYLATE COPOLYMERS

BACKGROUND OF THE INVENTION

The present invention relates to pressure-sensitive adhesive compositions; and more particularly to water vapor permeable pressure-sensitive adhesive compositions.

The present invention also relates to pressure-sensitive adhesive compositions suitable for medical and/or surgical bandage sheeting materials, including adhesive tapes.

The present invention more particularly relates to water vapor permeable, pressure-sensitive adhesives for medical and/or surgical bandage sheeting materials incorporating modified acrylate copolymers.

The present invention further relates to a pressure-sensitive adhesive which will cause minimum maceration or tissue damage of contacted skin areas, when used to attach a medical or surgical dressing or adhesive tape or bandage thereto.

The present invention still further relates to a water vapor permeable, pressure-sensitive adhesive composition which is at once both convenient to use and economical to manufacture.

The use of pressure-sensitive adhesive-coated sheet materials in the form of adhesive tapes, medical and surgical bandages, and surgical drapes for the management of skin wounds in order to protect the subject wounds from trauma, superficial dirt and bacterial contamination, also to absorb wound exudate, and to limit movement of tissues, is a widely practiced and well-accepted medical practice.

For many years, the pressure-sensitive adhesives that have been used for attachment of these dressing materials to the skin surface were natural rubber based, and therefore they contained the usual chemical additives, such as resins, plasticizers, anti-oxidants, etc. The foregoing listed chemical additives, in addition to others, are potentially irritating to human skin. In addition, as the pressure-sensitive adhesive and, in some cases, the dressing materials were occlusive and water vapor non-permeable by nature, the adhesive sheet materials led to water accummulation under them following their emplacement.

The accummulated water would then over-hydrate and soften the outer layers of the skin (stratum corneum), thus causing what is referred to as skin maceration. Further, the stratum corneum of the then macerated skin is readily further damaged when the pressure-sensitive adhesive-coated sheet material is removed. Therefore, in order to prevent the widely prevalent moisture-caused maceration of skin, the pressure-sensitive adhesive-coated sheet materials should preferably be composed of water vapor permeable adhesive substrate backings and non-irritating pressure-sensitive adhesives.

Many of the modern surgical adhesive dressings and bandages employ an acrylic-based pressure-sensitive adhesive, which is much more permeable to water than the prior art rubber-based occlusive adhesive compositions. Although acrylic-based pressure-sensitive adhesives are less traumatic to human skin than those which are rubber-based, they are not without their inherent disadvantages. Especially in applications where the pressure-sensitive adhesive-coated dressing sheet material is repeatedly applied to and then removed from the same area of the skin surface, e.g., as in the changing of a medical or surgical dressing, or when in place over a prolonged period of time, a significant local skin damage or water-induced maceration can result.

The present invention pressure-sensitive adhesive is a copolymeric composition, having improved pressure-sensitive adhesive properties and enhanced water vapor permeability. It is comprised of about 79 to 89 percent by weight of n-butyl acrylate, from about 10 to 20 percent by weight of a hydrophilic N-vinyl lactam, and from about 1 to 5 percent by weight of an acidic comonomer.

Pressure-sensitive adhesive compositions are commonly applied to the flexible backing or tape on which they are supported during use by coating them in the form of a solution or dispersion in a suitable vehicle such as an organic solvent or water, and evaporating the vehicle, or by coating them in the form of a hot melt free from vehicle. In order to be useful, pressure-sensitive adhesive compositions must possess not only good tack but also good cohesive strength and the desired high degree of adhesion. All of these properties are generally interdependent, a change in one usually causing a change in the others.

Conventional acrylic-based pressure-sensitive adhesive compositions are generally single component materials, comprised of copolymers of long chain alkyl acrylate ($C_4$–$C_8$) esters with polar monomers such as acrylic acid, acrylonitrile, acrylamide, etc. Optional modifying monomers which may also be copolymerized with alkyl acrylate esters are methyl or ethyl acrylate, alkyl ($C_1$–$C_4$) methacrylates, styrene, vinyl acetate, etc.

In order to achieve optimum cohesive and adhesive properties of the copolymer, a proper balance of its molecular weight (usually very high, from about 800,000 to more than about 1,000,000 mw), its polar character, and a glass transition temperature ($T_G$) ranging from about $-25°$ C. to $-70°$ C., is necessary.

R. F. Peck (U.K. Pat. GB No. 2,070,631A) teaches the copolymerization of n-butyl acrylate, 2-ethylhexyl acrylate and acrylic acid to produce a polyacrylate having a K-value of from 90 to 110 claimed to result in a satisfactory water vapor permeability for use with medical dressings.

E. Schonfeld (U.S. Pat. No. 4,140,115) has proposed the incorporation of a polyol, such as polyoxyalkylene glycol, in the acrylic adhesive mass for use in surgical and/or medical bandages or tapes, which are claimed to result in less skin damage upon their removal.

Ono, et al, (U.S. Pat. No. 3,975,570) has proposed to improve the water vapor permeability of conventional acrylic pressure-sensitive adhesives by blending with them hydroxyethyl cellulose.

K. R. Shah (the present inventor) in his U.S. Pat. No. 4,337,325, has described blending alkyl acrylate-acrylic acid copolymers with certain proportions of N-vinyl lactam homopolymers and copolymers to obtain pressure sensitive adhesives having increased water vapor permeabilities.

H. Reinhard, et al, (U.S. Pat. No. 3,725,122) have disclosed a pressure sensitive adhesive comprising a copolymer of primary and/or secondary alkyl acrylate ($C_4$–$C_{12}$) esters, of which at least 25 percent are derived from alkanols having 6 to 12 carbon atoms, tertiary alkyl ($C_4$–$C_{12}$) esters, N-vinyl pyrrolidone (1 to 10 percent by weight), and olefinically unsaturated monomers (such as acrylic acid, acrylamide, etc.) containing reactive groups.

However, it should be noted that the presence of small amounts (i.e. 10 percent) of hydrophilic N-vinyl pyrrolidone, and the presence of hydrophobic long chain ($C_6$–$C_{12}$) alkyl acrylate moities in the above-discussed copolymeric compositions, would not be expected to impart enhanced water vapor permeability to them.

In Martens, et al, (U.S. Pat. No. 4,181,752), a process for the free radical polymerization of acrylic monomers by means of ultraviolet irradiation under controlled conditions in order to prepare pressure sensitive adhesives is described and claimed. N-vinyl pyrrolidone and acrylic acid have been mentioned in Martens, et al, as monomers copolymerizable with alkyl acrylates by the irradiation process. However, copolymers of n-butyl acrylate, N-vinyl pyrrolidone, and acrylic acid as described and claimed in the present invention were not taught or considered by the above-discussed inventors.

SUMMARY OF THE INVENTION

An object of the present invention is to provide an improved pressure-sensitive adhesive composition.

A further object of the present invention is to provide an improved pressure-sensitive adhesive composition suitable for medical and/or surgical bandage sheeting materials, including adhesive tapes.

Still yet another object of the present invention is to provide an enhanced water vapor permeable, pressure-sensitive adhesive composition for coating onto medical and surgical bandage sheet materials, which incorporates modified acrylic copolymers.

It is also yet another object of the present invention to provide an enhanced water vapor permeable, pressure-sensitive adhesive, which will cause minimum maceration or damage of contacted skin areas when utilized to attach a medical or surgical dressing or adhesive bandage thereto.

It is still yet a further object of the present invention to provide such a water vapor permeable, pressure-sensitive adhesive which is at once both convenient to use and economical to manufacture.

In order to accomplish the aforestated objectives, and others as well, an enhanced water vapor permeable, pressure-sensitive adhesive composition, suitable for coating onto medical and/or surgical sheet dressing materials and the like, and incorporating modified copolymers of n-butyl acrylate containing N-vinyl 2-pyrrolidone and acrylic acid, is described. The present invention yields a pressure-sensitive adhesive composition having enhanced water vapor transmission rates, which may lead to a concomittant reduction in skin lesions that were previously attendant upon the accummulation of moisture under conventional medical and surgical dressings.

DESCRIPTION OF THE PREFERRED EMBODIMENT

The monomeric constituents of the copolymeric compositions of the present invention have been specifically selected in order to obtain an optimum balance of the adhesive, cohesive and hydrophilic properties that are necessary to yield a suitable water vapor permeable, pressure-sensitive adhesive composition.

The butyl acrylate component of the preferred copolymer of the present invention provides the requisite pressure-sensitive tack. The combination of the N-vinyl lactam and acidic comonomers will provide the necessary cohesiveness in the copolymer, by increasing its glass transition temperature and by the hydrogen bonding interactions. The presence of the same highly polar and hydrophilic units in the copolymer also serves to enhance its adhesiveness and relatively high water vapor permeability characteristics.

Further, molecular weights of the preferable copolymer should be optimized from about 200,000 to about 500,000, in order to obtain the required cohesive-adhesive balance of its properties. Very high molecular weights of the copolymers should be avoided, because it will result in poor tack characteristics in these copolymers, whereas very low molecular weight copolymers will yield cohesively weak pressure-sensitive adhesives.

The N-vinyl lactam monomers which may be used in preferred embodiments of the present invention include: 1-vinyl-2-pyrrolidone, 1-vinyl-5-methyl 2-pyrrolidone, 1-vinyl-2-piperidinone, and 1-vinyl $\epsilon$-caprolactam.

The acidic comonomers suitable for preparation of the copolymer of the present invention include: acrylic acid, methacrylic acid, itaconic acid, and 2-sulfoethyl methacrylate.

The relative proportions of the three types of monomers utilized in the instant invention copolymer may vary within certain limits.

The n-butyl acrylate component may vary from about 79 to about 89 percent by weight, based on the total weight of the copolymer yield. The hydrophilic N-vinyl lactam may vary from about 10 to about 20 percent by weight of the copolymer. Finally, the ethylenically unsaturated monomer containing an acidic group, may vary from about 1 to about 5 percent by weight of the copolymer.

The copolymeric compositions of the present invention may be suitably coated onto the conventional water-permeable sheeting material or substrates employed in the manufacture of adhesive tapes and/or medical and surgical dressing sheets. For example, suitable water vapor permeable substrates for the pressure-sensitive adhesive composition of the present invention are polymeric membranes such as polyurethanes, or Copel TM (General Electric Company) a copolymer of polycarbonate and polysiloxane, perforated vinyls, or microporous polyethylene and polypropylene films, and woven and nonwoven webs of fibrous material, such as woven textile fabrics and nonwoven fabrics made from natural and/or synthetic fibers.

Such coatings may be deposited onto the substrates by casting a solution of the copolymer composite onto the backing materials, and then removing the solvent by means of evaporation in a drying oven at a suitable temperature.

In the event that the desired bandage substrate is either heat- and/or solvent-sensitive, as for example, polyurethane and plasticized vinyl films, the copolymer solution is first cast onto a release liner, then dried, and finally laminated onto the desired substrate by the use of sufficient pressure between two laminating rolls. The release paper may then be removed prior to its use.

Continuous, non-porous 1 mil thick coatings of the copolymers of this invention will exhibit enhanced water vapor transmission rates of greater than 1,000 gms/meter$^2$/24 hours at 40° C. and 80% relative humidity.

The probe tack characteristic was determined by means of a Polyken Probe Tack Tester, sold by the Polyken Division of The Kendall Company, and as described in U.S. Pat. No. 3,214,971 having the following four functional parts: (1) a cylindrical steel probe attached to the compression loaded spring of (2) a series L Hunter mechanical force gauge (Hunter Spring Company, Brochure 750/FG, revised February 1961), (3) an annulus having an opening slightly larger than the diameter of the probe and (4) a carrier for the annulus which moves down to bring the annulus around the probe and then up to remove the annulus therefrom.

The carrier moves at a speed of 0.1 inch per second. At the beginning of the test, the carrier is at its uppermost point of travel and the annulus rests upon the carrier so that the opening in the annulus is in line with the probe positioned beneath it. In carrying out the test, a strip of tape is placed upon the annulus, adhesive side down, and spanning the annulus opening. As the carrier is driven downwardly by the synchronous motor, the adhesive surface exposed through the opening is brought into contact with the flat surface of the probe so that the tape and the annulus attached thereto are suspended on the probe as the carrier continues farther on its downward path. The carrier then reverses its movement returning to pick up the annulus, thereby separating the tape from the probe surface. Separation begins after one second contact between the probe and the adhesive. The force required to separate the tape from the probe is recorded on a gauge. The recorded value is the probe tack value. Measurements were made employing a loading of 100 grams/cm$^2$.

The 180° peel adhesion test basically involves determining resistance of pressure-sensitive tape/stainless steel laminates to being delaminated at a 180° angle and at a rate of 12 inches per minute. The test laminates are consistently prepared by laying the adhesive tape onto the cleaned stainless steel plates and using only the pressure from two passes of a 5 pound roller to complete lamination. The peel test is conducted 15 minutes after rolling.

Flat bar creep is measured as the time required for a 1" wide and 2" long tape, laminated to a stainless steel plate, to slide ½" under a 1000 gram weight hung in essentially vertical position at 100° F. The adhesive tape/stainless steel laminate is prepared by the same method as the peel strength test laminates.

The water vapor transmission rate (W) of a polymer film, having a specified thickness is defined by the following equation:

$$W = g/A \times t$$

where g is the weight of water vapor transported in time t through a film area A at a given temperature and relative humidity difference.

For the purpose of determination of water permeability of the copolymer, a supported 1 mil thick film of the copolymer is prepared by casting a solution of the copolymer on a release paper, then removing the solvent by evaporation, and transferring the dried film to a plastic netting material, such as Delnet ™ Kx215 (Hercules, Inc.), which has an open area of greater than 85%. The water vapor permeability of the supported copolymer film is determined by the ASTM E96-66-Desicant method carried out as follows. The supported copolymer film is fastened over the mouth of a dish, which contains a desicant (granular calcium chloride). The assembly is placed in an atmosphere of 80% relative humidity and a constant temperature of 40° C. The weight of the assembly is periodically recorded, and the gain in weight is used to calculate the rate of water vapor movement through the copolymer film.

The present invention is further exemplified below by an example thereof in accordance with the preferred embodiments of the invention. In the following example, and throughout this application, all parts and percentages are by weight unless otherwise indicated, and all temperatures are reported in degrees Celsius, unless otherwise specified.

EXAMPLES

Example 1

In a 2-liter resin kettle equipped with a stirrer, a thermometer, a condenser, and a nitrogen inlet tube, was placed a 200 g portion of a monomeric solution consisting of 420 g n-butyl acrylate, 62.75 g. N-vinyl 2-pyrrolidone, 14.93 g. acrylic acid, 500 g. ethyl acetate, 747 mg. azobisisobutyronitrile, and 359 mg. n-dodecanethiol.

After a continuous purge of the reaction vessel with nitrogen was started, the monomeric mixture was then heated and allowed to reflux for 20 to 30 minutes, during which period the viscosity of the reaction mixture increased substantially. The remainder of the monomeric solution was then gradually added to the viscous reaction product under constant agitation over a period of 2 hours, while reflux of the solvent was maintained. After addition of the monomeric solution was completed, the reaction mixture was maintained under agitation and solvent reflux for an additional period of 15 minutes.

Percent non-volatiles in the final product thus obtained was 47 percent; polymerization conversion was 97 percent; and the product viscosity was 25,600 centipose (Brookfield, spindle #3, @2.5 RPM and 22° C.). The weight, average molecular weight of the copolymer, determined by gel permeation chromatography, was 262,000. Water vapor transmission rate of 1 mil thick non-porous film of the dried copolymer was greater than 1,430 g/meter$^2$/24 hours @40° C. and 80% RH.

The copolymer solution thus prepared was then coated onto a smooth surface release-coated silicone paper and dried to yield a 1.1 mil thick copolymeric adhesive film, which was then transferred to a sheet of polyurethane film, also 1.1 mil thick. The adhesive coated sheet had probe tack value of 130 g/cm$^2$, adhesion to steel of 26.5 oz/inch width, and flat bar creep at 100° F. of 4.5 hours.

What is claimed is:

1. A water vapor permeable, pressure-sensitive adhesive composition comprising:
an adhesive copolymer having a molecular weight from about 200,000 to about 500,000, further comprising:
   (a) from about 79 to 89 percent by weight of n-butyl acrylate;
   (b) from about 10 to 20 percent by weight of a hydrophilic N-vinyl lactam, selected from the group consisting of 1-vinyl-2-pyrrolidone, 1-vinyl-5-methyl-2-pyrrolidone, 1-vinyl-2-piperidinone and 1-vinyl-ε-caprolactum; and
   (c) from about 1 to 5 percent by weight of an acidic comonomer selected from the group consisting of acrylic acid, methacrylic acid, itaconic acid, and 2-sulfoethyl methacrylate; and
said adhesive copolymer in the form of a coating of about 1.0 mil thickness having water vapor transmission rates of greater than 1,000 gms/meter$^2$/24 hours at 40° C. and 80 percent relative humidity; and further exhibiting a probe tack value of about 130 mg/cm$^2$, adhesion to steel of about 26.5 oz/inch width, and flat bar creep at 100° F. of about 4.5 hours.

2. The water vapor permeable, pressure-sensitive adhesive composition of claim 1 comprising
an adhesive copolymer, further comprising:
 (a) from about 79 to 89 percent by weight of n-butyl acrylate;
 (b) from about 10 to 20 percent by weight of N-vinyl-2-pyrrolidone; and
 (c) from about 1 to 5 percent by weight of acrylic acid; and
said adhesive copolymer in the form of a coating of about 1.0 mil thickness, having water vapor transmission rates of greater than 1,000 gms/meter$^2$/24 hours at 40° C. and 80 percent relative humidity; and further exhibiting a probe tack value of about 130 mg/cm$^2$, adhesion to steel of about 26.5 oz/inch width, and flat bar creep at 100° F. of about 4.5 hours.

3. A water vapor permeable, pressure-sensitive adhesive, according to claim 1, wherein the N-vinyl lactam is N-vinyl-2-pyrrolidone.

4. A water vapor permeable, pressure-sensitive adhesive composition comprising
an adhesive copolymer having a molecular weight from about 200,000 to about 500,000, further comprising:
 (a) about 84 percent by weight of n-butyl acrylate;
 (b) about 13 percent by weight of N-vinyl-2-pyrrolidone; and
 (c) about 3 percent by weight of acrylic acid; and
said adhesive copolymer in the form of a coating of about 1.0 mil thickness having water vapor transmission rates of greater than 1,000 gms/meter$^2$/24 hours at 40° C. and 80 percent relative humidity; and further exhibiting a probe tack value of about 130 mg/cm$^2$, adhesion to steel of about 26.5 oz/inch width, and flat bar creep at 100° F. of about 4.5 hours.

* * * * *